(12) United States Patent
Levy et al.

(10) Patent No.: US 12,053,610 B2
(45) Date of Patent: Aug. 6, 2024

(54) SYSTEM FOR CONTROLLED DELIVERY OF MEDICAL FLUIDS

(71) Applicants: Kimberley Levy, Fort Myers, FL (US); Frank Levy, Fort Myers, FL (US)

(72) Inventors: Kimberley Levy, Fort Myers, FL (US); Frank Levy, Fort Myers, FL (US)

(*) Notice: Subject to any disclaimer, the term of this patent is extended or adjusted under 35 U.S.C. 154(b) by 1624 days.

(21) Appl. No.: 15/672,691

(22) Filed: Aug. 9, 2017

(65) Prior Publication Data

US 2017/0368254 A1   Dec. 28, 2017

Related U.S. Application Data

(63) Continuation of application No. 14/703,186, filed on May 4, 2015, now Pat. No. 9,757,508, which is a continuation of application No. 13/065,621, filed on Mar. 25, 2011, now Pat. No. 9,050,401.

(60) Provisional application No. 61/395,892, filed on May 19, 2010.

(51) Int. Cl.
| | |
|---|---|
| *A61M 39/22* | (2006.01) |
| *A61M 5/00* | (2006.01) |
| *A61M 5/19* | (2006.01) |
| *A61M 5/178* | (2006.01) |

(Continued)

(52) U.S. Cl.
CPC ............... *A61M 5/007* (2013.01); *A61M 5/19* (2013.01); *A61M 39/223* (2013.01); *A61M 2005/006* (2013.01); *A61M 2005/1787* (2013.01); *A61M 2039/0009* (2013.01); *A61M 2039/0027* (2013.01); *A61M 39/24* (2013.01); *A61M 2202/0225* (2013.01); *F04C 2270/0421* (2013.01)

(58) Field of Classification Search
CPC .......... A61M 39/223; A61M 2039/229; A61M 5/16827
See application file for complete search history.

(56) References Cited

U.S. PATENT DOCUMENTS

| | | | |
|---|---|---|---|
| 3,004,686 A | 10/1961 | McKee | |
| 3,048,192 A * | 8/1962 | Murphy, Jr. | ........ A61M 39/223 137/625.42 |
| 4,219,021 A | 8/1980 | Fink | |

(Continued)

FOREIGN PATENT DOCUMENTS

| | | |
|---|---|---|
| EP | 2468204 A1 | 6/2012 |
| JP | H06-013845 U | 2/1994 |

*Primary Examiner* — Emily L Schmidt
(74) *Attorney, Agent, or Firm* — Welsh Flaxman & Gitler LLC (57) ABSTRACT

A system for controlled delivery of medical fluids to a patient includes an inlet conduit attached to a source of a medical fluid and an outlet conduit connected to the patient. The inlet and outlet conduits are interconnected by a multiple stage control valve assembly and a pair of syringes. The control valve assembly is alternated between a first state wherein the inlet conduit communicates with a first syringe for transmitting fluid from the source to the first syringe, a second state wherein the first syringe communicates with a second syringe and is isolated from the inlet conduit and the outlet for transmitting fluid from the first syringe to the second syringe, and a third state wherein the second syringe communicates with the outlet and is isolated from the inlet and the first syringe for transmitting fluid from the second syringe to the patient through the outlet.

12 Claims, 7 Drawing Sheets

(51) Int. Cl.
  *A61M 39/00* (2006.01)
  *A61M 39/24* (2006.01)

(56) References Cited

U.S. PATENT DOCUMENTS

| | | |
|---|---|---|
| 4,950,230 A | 8/1990 | Kendell |
| 5,135,026 A | 8/1992 | Manska |
| 5,195,963 A | 3/1993 | Yafuso et al. |
| 5,345,932 A | 9/1994 | Yafuso et al. |
| 6,315,762 B1 | 11/2001 | Recinella et al. |
| 2001/0044618 A1 | 11/2001 | Recinella et al. |
| 2002/0017328 A1 | 2/2002 | Loo |
| 2003/0181850 A1 | 9/2003 | Diamond et al. |
| 2005/0000981 A1 | 1/2005 | Peng et al. |
| 2007/0104616 A1 | 5/2007 | Keenan et al. |
| 2007/0111298 A1 | 5/2007 | Muller et al. |
| 2008/0167621 A1 | 7/2008 | Wagner et al. |
| 2009/0062741 A1 | 3/2009 | Smith et al. |
| 2009/0247985 A1 | 10/2009 | Melsheimer et al. |
| 2011/0011474 A1* | 1/2011 | Duncan ............... F16K 11/0853 137/625.47 |
| 2011/0152850 A1 | 6/2011 | Niedbala et al. |
| 2011/0218411 A1 | 9/2011 | Keenan et al. |

\* cited by examiner

SYSTEM FOR CONTROLLED DELIVERY OF MEDICAL FLUIDS

RELATED APPLICATION

This application is a continuation of U.S. patent application Ser. No. 14/703,186, entitled "SYSTEM FOR CONTROLLED DELIVERY OF MEDICAL FLUIDS", filed May 4, 2015, which is a continuation of U.S. patent application Ser. No. 13/065,621, filed Mar. 25, 2011, entitled "SYSTEM FOR CONTROLLED DELIVERY OF MEDICAL FLUIDS", which is now U.S. Pat. No. 9,050,401, which claims the benefit of U.S. Provisional Application Ser. No. 61/395,892, filed May 19, 2010.

FIELD OF THE INVENTION

This invention relates to a system for safely delivering a controlled volume of a medical fluid to a patient and, more particularly to a system for delivering a controlled flow of carbon dioxide ($CO_2$) or other contrast fluid in order to obtain radiological images.

BACKGROUND OF THE INVENTION

Various types of medical equipment have been utilized to deliver controlled volumes of liquid and gaseous substances to patients. One field that involves the administration of such fluids is radiology, wherein a small amount of carbon dioxide gas or an alternative contrast media is delivered to the vascular system of the patient in order to displace the patient's blood and obtain improved images of the vascular system. Traditionally, this has required that the $CO_2$ or other media first be delivered from a pressurized cylinder to a syringe. The filled syringe is then disconnected from the cylinder and reconnected to a catheter attached to the patient. If additional $CO_2$ is needed, the syringe must be disconnected from the catheter and reattached to the cylinder for refilling. Not only is this procedure tedious and time consuming, it presents a serious risk of introducing air into the $CO_2$ or contrast fluid at each point of disconnection. Injecting such air into the patient's blood vessels can be extremely dangerous and even fatal.

Recinella et al., U.S. Pat. No. 6,315,762 discloses a closed delivery system wherein a bag containing up to 2,000 ml of carbon dioxide or other contrast media is selectively interconnected by a stopcock to either the chamber of a syringe or a catheter attached to the patient. Although this system does reduce the introduction of air into the administered fluid caused by disconnecting and reconnecting the individual components, it still exhibits a number of shortcomings. For one thing, potentially dangerous volumes of air are apt to be trapped within the bag. This usually requires the bag to be manipulated and flushed multiple times before it is attached to the stopcock and ultimately to the catheter. Moreover, this delivery system does not feature an optimally safe and reliable, foolproof operation. If the stopcock valve is incorrectly operated to inadvertently connect the carbon dioxide filled bag or other source of carbon dioxide directly to the patient catheter, a dangerous and potentially lethal volume of $CO_2$ may be delivered suddenly to the patient's vascular system. It is medically critical to avoid such $CO_2$ flooding of the blood vessels.

SUMMARY OF THE INVENTION

It is therefore an object of the present invention to provide a system for safely and reliably delivering a controlled dosage of a fluid to a medical patient.

It is a further object of this invention to provide a fluid (i.e. liquid or gas) delivery system that is particularly effective for use in administering $CO_2$ or other contrast media in a controlled manner to a patient's vascular system to provide improved contrast for radiological imaging.

It is a further object of this invention to provide a fluid delivery system and particularly a $CO_2$/contrast media delivery system that prevents potentially dangerous amounts of air from entering the fluid and thereby being administered to the patient.

It is a further object of this invention to provide a fluid delivery system that prevents accidentally flooding of the patient's vascular system with carbon dioxide or other administered gases or liquids under positive pressure.

It is a further object of this invention to provide a fluid delivery system exhibiting a failsafe and foolproof operation, which permits only reliable and accurately controlled dosages of a medical fluid to be administered to a patient.

It is a further object of this invention to provide a fluid delivery system that may be used safely and effectively with virtually any source of carbon dioxide or other medical fluid regardless of the pressure or environment under which that fluid is maintained.

It is a further object of this invention to provide a fluid flow system that prevents an administered medical fluid from flowing in an unintended direction through the system.

This invention results from a realization that an improved, foolproof system for safely delivering controlled amounts of a medical fluid such as $CO_2$ or other contrast media to a patient may be accomplished by utilizing a multi-part valve that delivers the fluid in precisely controlled amounts sequentially through a series of syringes such that it is impossible to directly connect the fluid source to the patient. At the same time, the delivery system does not have to be disconnected and reconnected during the administration of medical fluid. This greatly reduces the intrusion of air into the system and the fluid being administered.

This invention features a system for controlled delivery of a medical fluid from a source of such fluid to a patient. The system includes an inlet conduit that is communicably joined to a source of the medical fluid and an outlet conduit that is communicably joined to the patient. First and second syringes are intermediate the inlet and outlet conduits. A control valve assembly interconnects the inlet and outlet conduits as well as the intermediate first and second syringes. The control valve assembly is alternatable between first, second, and third states. In the first state, the inlet communicates with the first syringe for transmitting fluid from the source to the first syringe. In the second state, the first syringe communicates with the second syringe and is isolated from the inlet and the outlet conduits for transmitting fluid from the first syringe to the second syringe. In the third state, the second syringe communicates with the outlet conduit and is isolated from the inlet conduit and the first syringe. This allows fluid to be transmitted from the second syringe to the patient through the outlet conduit.

In one embodiment, the valve assembly includes a valve body having aligned inlet and outlet ports that are communicably connectable to the inlet and outlet conduits respectively. The valve body further includes a pair of first and second intermediate ports that extend axially transversely to the inlet and outlet ports and transversely to each other. A stopcock is mounted rotatably within the valve body and includes an angled channel having a pair of communicably interconnected channel segments that extend axially at an acute angle to one another. The channel segments of the stopcock are interconnected at an angle that is generally equivalent to the angle formed between each adjacent pair of non-aligned ports in the valve body such that the stopcock is rotatable to align the channel segments with a selected adjacent pair of the non-aligned ports to permit fluid communication between those ports. Each of the intermediate ports is connectable to a respective syringe. The stopcock is selectively adjusted between first, second and third positions. In the first position, the channel segments communicably interconnect the inlet port and a first one of the intermediate ports. Fluid introduced through the inlet conduit portion is thereby transmitted through the inlet port and the channel of the stopcock to the first intermediate port. This port directs the fluid to a first syringe attached thereto. In the second valve position, the stopcock aligns the channel segments with the first and second intermediate ports respectively. This isolates the fluid in the first syringe from both the inlet and outlet conduits. The first syringe is operated to direct the fluid through the first intermediate port, the stopcock channel and the second intermediate port into a second syringe joined to the second intermediate port. In the third valve position, the stopcock is rotated to align the channel segments with the second intermediate port and the outlet port respectively. This isolates the fluid in the second syringe from the fluid source, the inlet port and the first intermediate port. The second syringe is then operated to drive the fluid through the second intermediate port, the channel of the stopcock and the outlet port to the outlet conduit. The outlet conduit directs this fluid to the patient.

The respective longitudinal axes of the inlet and outlet ports are aligned. The first and second intermediate ports may include respective longitudinal axes that form an angle of substantially 60 degrees with one another. The first intermediate port may form an axial angle of substantially 60 degrees with the longitudinal axis of the inlet port and, similarly, the axis of the second intermediate port may form an axial angle of substantially 60 degrees with the longitudinal axis of the outlet port.

The angular channel formed in the stopcock preferably features channel segments with respective longitudinal axes that form an angle of substantially 60 degrees. As sued herein, "substantially 60 degrees" means that the angles are either precisely or approximately 60 degrees such that the channel segments of the stopcock are communicably and selectively interengagable with a respective pair of adjoining, non-aligned ports in each of the three valve positions. Alternative angles may be features when the inlet and outlet conduits are not aligned. A lever is attached to the valve body for adjusting the stopcock between the three alternate valve positions.

The inlet conduit may include a fitting for sealably interconnecting to a source of medical fluid. The fitting may include a one-way valve for limiting the flow of fluid to a single direction from the source of fluid to the valve assembly and for preventing flow in the opposite direction. The inlet conduit may include coiled tubing. A second one-way valve may be mounted within the inlet port of the valve body for restricting fluid flow from the valve body to the inlet conduit.

The valve assembly may further include a one-way outlet valve mounted in the outlet port for restricting fluid to flow to a single direction from the outlet port to the outlet conduit and for preventing fluid flow in the opposite direction. A second coil section of tubing is formed in the outlet section.

The outlet conduit may carry a downstream valve for bleeding and/or purging fluid and/or for administering an additive fluid to the controlled fluid. The outlet' conduit may be communicably connected to a patient catheter. An additional one-way valve may be carried by the downstream valve to restrict flow of the fluid through the downstream valve to a single direction from the outlet conduit to the patient catheter.

The outlet conduit may alternatively be connected to a downstream fitting having a one-way valve for directing fluid flow from the outlet conduit through the fitting to the patient. The fitting may include a port that allows fluid to be purged or flushed from the catheter. The port may also be used to deliver medications through the fitting and the catheter to the patient. The downstream fitting may be connected to a medication or fluid administering syringe through a conduit that is attached to the downstream fitting. Respective Luer™ fittings may be used to interconnect the inlet and outlet conduits to the control valve. A Luer™ fitting may also be employed to connect the downstream valve or fitting to the catheter.

The system of this invention may alternatively feature sequential, multiple stage delivery of a medical fluid from a source to a patient through a pair of directional or multidirectional valves. A first such valve is operated to either deliver fluid from the source to a first syringe or to deliver fluid from the first syringe to the inlet of a second valve. The second valve is then operated to selectively deliver fluid from the first syringe through the second valve to a second syringe. Alternatively, the second valve may be operated to deliver the fluid from the second syringe to the downstream catheter or patient. A critical feature of this invention is that a precise volume or dosage of $CO_2$ or other medical liquid/gas is delivered sequentially in three distinct stages from the source to the patient. In each stage, the source, which is typically under pressure, remains totally isolated from the patient so that fluid is administered much more safely than in prior systems.

This invention further features a process for delivering medical fluid from a source of such fluid to a patient in controlled doses. The process involves providing inlet and outlet conduits that are connected respectively to a source of medical fluid and a patient. A control valve assembly and a pair of first and second syringes are interconnected between the inlet and outlet conduits. The control valve assembly is first operated to communicably join the fluid source and the first syringe and medical fluid is transmitted from the source to the first syringe. The control valve assembly is then adjusted to communicably join the first and second syringes while isolating the first syringe and the second syringe from the source of fluid. The first syringe is then operated to transmit medical fluid from the first syringe to the second syringe through the control valve assembly. The second syringe and the outlet conduit are then communicably joined by further adjusting the control valve assembly and the second syringe is operated to transmit medical fluid from the second syringe to the patient through the outlet conduit. The first syringe and the fluid source remain isolated from the second syringe.

DETAILED DESCRIPTION OF PREFERRED EMBODIMENTS

Other objects, features and advantages will occur from the following description of a preferred embodiment and the accompanying drawings, in which.

Figure 1:
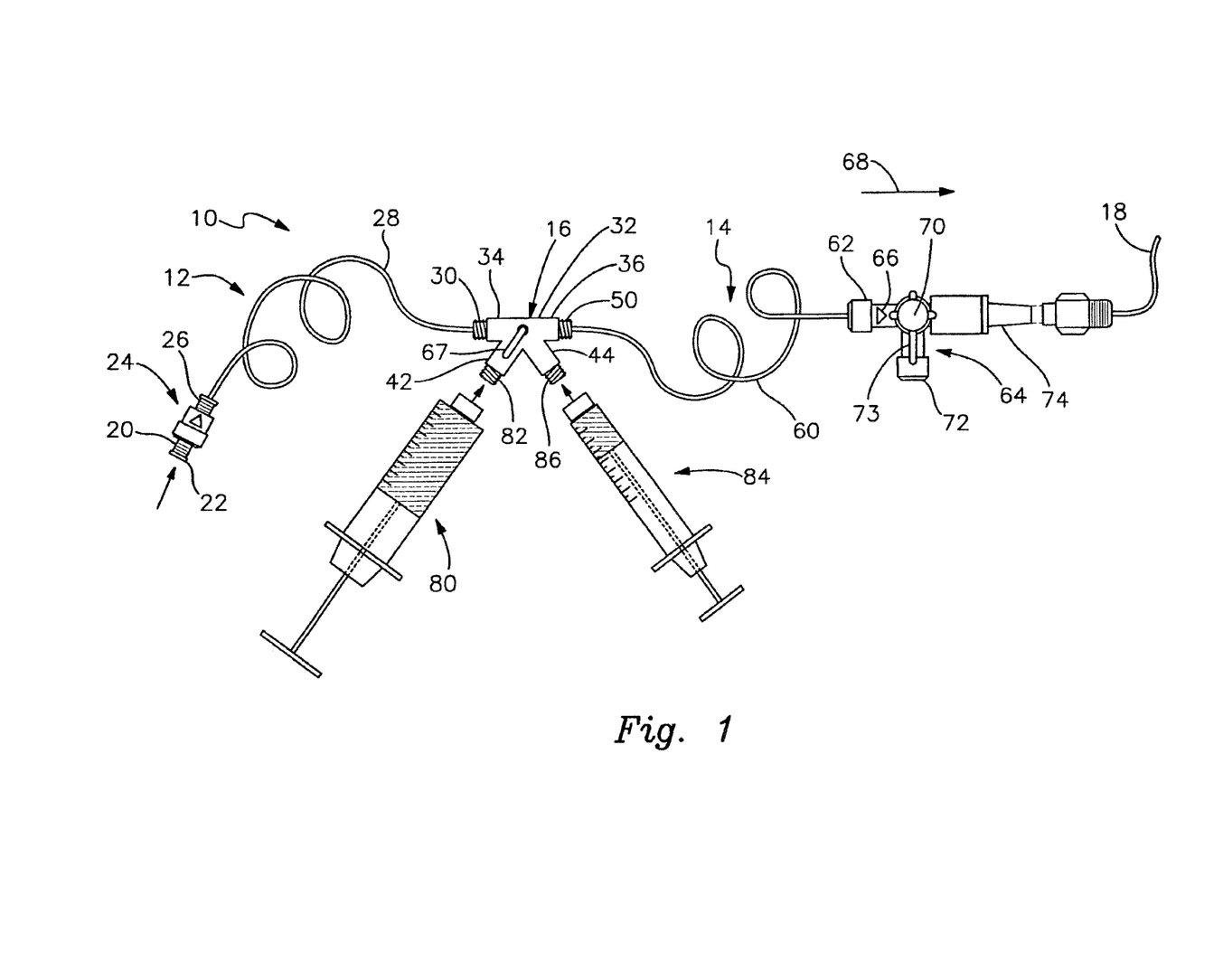
FIG. 1 is a somewhat simplified plan and partly schematic view of the system for controlled delivery of medical fluids in accordance with this invention.
Figure 2:
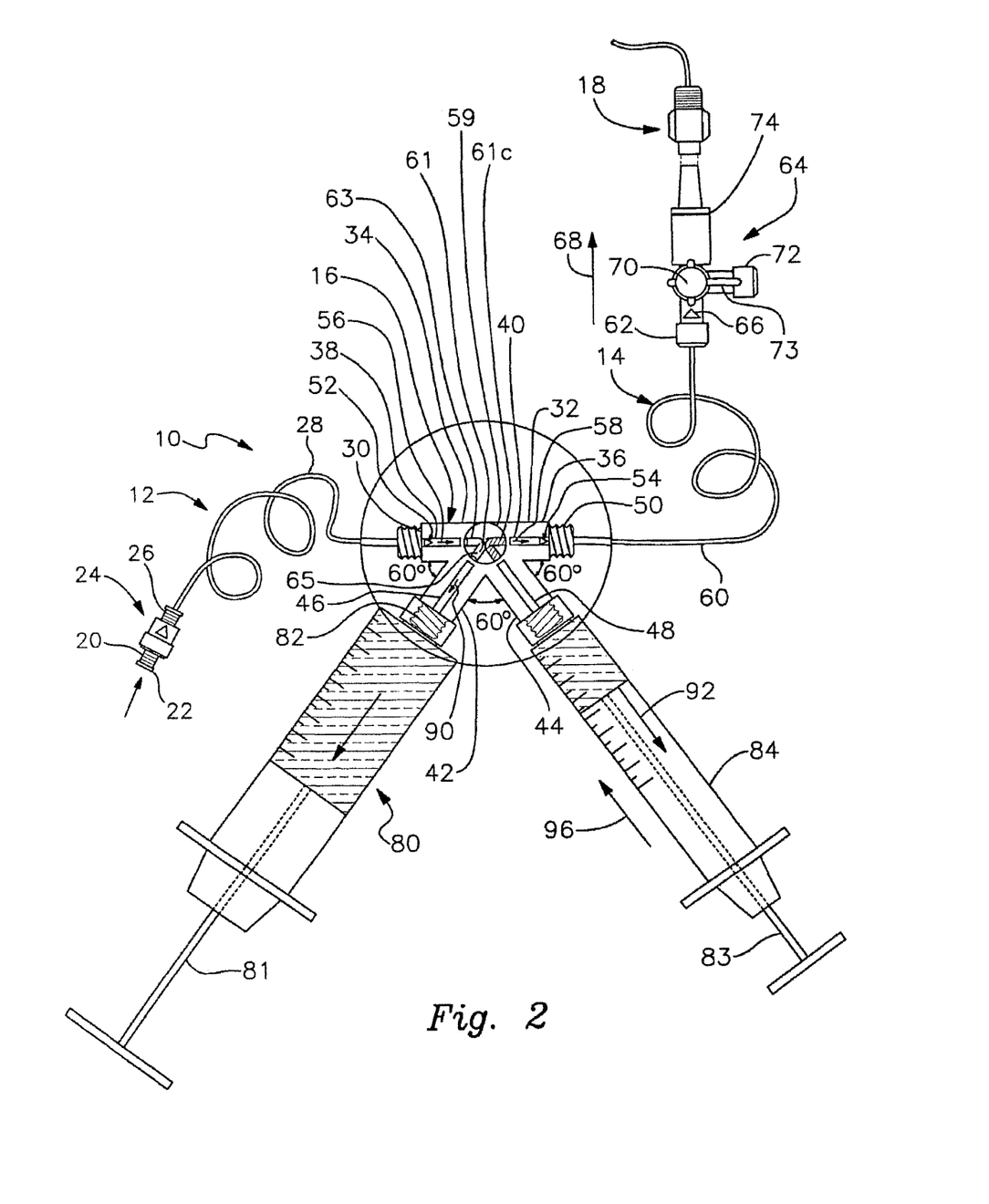
FIG. 2 is a view similar to FIG. 1 wherein the control valve assembly is enlarged for clarity and the internal construction of the valve assembly is illustrated.

There is shown in FIGS. 1 and 2 system 10 for delivering controlled dosages of a medical contrast fluid such as carbon dioxide ($CO_2$) for use in the radiological imaging of arteries and veins of a patient's vascular system. Although this is a preferred application for system 10, it should be understood that the system may be used for the controlled delivery of various other types of liquids and gases administered as part of assorted surgical and medical procedures. As used herein, the term "fluid" should be understood to include various types of medical liquids and gases. By the same token, when "gas" is used herein, it should be understood that such description is likewise applicable to various types of medical liquids.

System 10 includes an inlet conduit 12 and an outlet conduit 14 interconnected by a three-stage K-valve shaped control assembly 16. Inlet conduit 12 communicably interconnects a source of carbon dioxide or other medical fluid (not shown) with valve assembly 16. Outlet conduit 14 likewise communicably interconnects a discharge end of valve assembly 16 with a catheter 18 that is, in turn, operably connected to a patient, not shown.

Inlet conduit 12 includes a Luer™ fitting 20 having a G-tube seal 22, which is selectively attached to the source of medical fluid, such as the $CO_2$ source. It should be understood that system 10 may be used with various sources of carbon dioxide including, but not limited to, pressurized tanks, bags and the $CO_2$mmander® manufactured by PMDA, LLC of North Fort Myers, Florida. The specific source of carbon dioxide or other medical fluid is not a limitation of this invention. A one-way directional valve 24 with a Luer™ fitting 26 is communicably joined to fitting 20. Fitting 26 is, in turn, communicably joined to a coiled medical tube 28 having a length of approximately 18". Various alternative lengths may be employed within the scope of this invention. The distal end of tube 28 carries a Luer™ fitting 30.

Three-stage control valve assembly 16 includes a generally K-shaped valve body 32, which is preferably composed of various medical grade plastics, metals and/or metal alloys. Typically, the valve body includes a molded or otherwise unitary construction. The valve body features four fluid transmitting ports 38, 46, 48 and 40. More particularly, valve body 32 includes aligned intake and discharge segments 34 and 36, respectively, which, as best shown in FIG. 2, include respective aligned internal inlet and outlet ports 38 and 40 respectively. The valve body also includes first and second transverse legs 42 and 44. Each leg extends at an angle of substantially 60 degrees from aligned branches 34 and 36 of valve body 32. Leg 42 includes an interior intermediate port 46 and leg 44 includes an interior intermediate port 48, which extend axially longitudinally through the respective legs 42 and 44. Ports 46 and 48 form transverse angles of substantially 60 degrees apiece with respective axial ports 38 and 40 of aligned branches 34 and 36.

Transverse legs 42 and 44 also extend at an angle of substantially 60 degrees to one another. By the same token, the longitudinal axes of ports 46 and 48 form an angle of substantially 60 degrees.

Valve assembly 16 further includes a stopcock 59 that, best shown in FIG. 2, which is rotatably mounted within valve body 32. The stopcock includes an angled channel 61 comprising communicably interconnected channel segments 63 and 65 having respective longitudinal axes that extend at an angle of approximately 60 degrees to one another. As used herein, "approximately 60 degrees" should be understood to mean that angle formed between the respective longitudinal axes of the channel segments 63, 65 is substantially equivalent to the angle formed between the longitudinal axes of respective pairs of the non-aligned adjacent ports of valve body 32 (e.g. respective pairs of ports 38, 46; 46, 48; and 48, 40). This enables the channel segments to be communicably aligned with a selected adjacent pair of the ports in the manner described more fully below. It should be understood that in alternative embodiments the ports and channel segments may have other corresponding angles. This is particularly applicable when the intake and discharge ports and/or the inlet and outlet conduits are not aligned.

As shown in FIG. 1, a valve lever 67 is mounted to valve body 32 for selectively rotating stopcock 59 into a selected one of three positions. For example, in FIG. 2, the stopcock is positioned with channel segments 63 and 65 of angled channel 61 communicably aligned with adjacent ports 38 and 46 respectively. Alternately, and as described more fully below, lever 67 may be manipulated to align the channel segments 63, 65 with respective ports 46 and 48 as indicated by the channel shown in phantom in position 61b. The lever may be likewise operated to align the respective channel segments with ports 48 and 40 as indicated by the angled channel (shown cross-hatched) in position 61c. Such selective positioning of the stopcock provides for controlled multiple stage delivery of fluid through valve 16 from inlet conduit 12 to outlet conduit 14. This operation is described more fully below.

Intake branch 34 of valve body 32 carries a complementary fitting for communicably interconnecting to Luer™ fitting 30 carried at the distal end of tubing 28. By the same token, discharge branch 36 of valve body 32 carries a complementary fitting for operably and communicably interconnecting with a Luer™ fitting 50 carried at the proximal end of outlet conduit 14. The remaining elements of the discharge conduit are described more fully below. Aligned ports 38 and 40 of valve body 32 include respective one-way valves 52 and 54, FIG. 2, which restrict or limit the flow of fluid within respective ports 38 and 40 to the direction indicated by arrows 56 and 58.

As further illustrated in FIGS. 1 and 2, outlet conduit 14 features a coiled medical tube 60 that is communicably interconnected between the Luer™ fitting 50 attached to discharge branch 36 of valve body 32 and a second Luer™ fitting 62, which is communicably joined to a downstream valve 64. The downstream valve includes a one-way valve 66 that restricts fluid flow from tubing 14 through valve 64 to the direction indicated by arrow 68. Valve 64 features a G-tube seal 73 that prevents air from intruding into the system prior to connection of valve 64. Valve 64 also includes a stopcock 70 that is rotatably operated within valve 64 to selectively bleed or purge fluid from system 10 through a port 72. Exit port 74 is selectively joined to patient catheter 18. Various alternative two and three port stopcocks may be used in the downstream valve.

A reservoir syringe 80 is communicably connected to axial port 46 of valve leg 42. Such interconnection is accomplished by a conventional Luer™ fitting 82, the details of which will be known to persons skilled in the art. Similarly, a second, draw-push syringe 84 is releasably attached by a Luer™ fitting 86 to the distal end of valve leg 44. This allows syringe 84 to be communicably interconnected with port 48 through second transverse leg 44. Syringes 80 and 84 are constructed and operated in a manner that will be known to persons skilled in the art.

System 10 is operated to deliver $CO_2$ or other medical fluid to a patient in a controlled and extremely safe and reliable manner. This operation is performed as follows.

Inlet conduit 12 is first interconnected between a source of carbon dioxide and intake branch 34 of valve body 32. Outlet section 14 likewise is communicably interconnected between discharge branch 36 of valve body 32 and downstream valve 64, which is itself attached to patient catheter 18. Syringes 80 and 84 are joined to valve legs 42 and 44 such that the syringes communicate with respective ports 46 and 48. The syringes should be selected such that they have a size that accommodates a desired volume of gas to be administered to the patient during the radiological imaging or other medical/surgical procedure.

After multistage K-valve assembly 16 has been interconnected between the inlet and outlet conduit 12 and 14, and following attachment of syringes 80 and 84 to respective valve legs 42 and 44, stopcock 59 is operated by valve lever 67 to align legs 63 and 65 of stopcock channel 61 with valve ports 38 and 46 respectively. See FIG. 2. The source of $CO_2$ is then opened or otherwise operated as required to deliver gas through inlet conduit 12 to valve 16. More particularly, the gas is delivered through one-way valve 24 and tubing 28 to the inlet port 38. One-way valve 52 prevents backflow of gas into the coil tubing 28. The $CO_2$ proceeds in the direction indicated by arrow 56 and is transmitted through angled stopcock channel 61 into port 46 of valve leg 42. From there, the gas proceeds as indicated by arrow 90 through the fitting 82 and into reservoir syringe 80. The $CO_2$ is introduced into reservoir syringe 80 in this manner until it fills the syringe.

When reservoir syringe 80 is filled, the operator manipulates lever 67, FIG. 1, and rotates the control valve into the second stopcock channel position represented in phantom by 61b in FIG. 2. In that position, channel segment 63 is communicably aligned with port 46 and channel segment 65 is communicably aligned with port 48. The plunger 81 of reservoir syringe 80 is pushed and the gas previously deposited into syringe 80 is transmitted through port 46 and the angled stopcock channel 61b into port 48. From there, the gas is introduced into draw-push syringe 84 as indicated by arrow 92. As this operation occurs, only the transverse, intermediate ports and their attached syringes are communicably connected. Both syringes remain completely isolated from both the inlet port 38 and the discharge or outlet port 40. By the same token, the source of carbon dioxide and communicably joined port 38 are isolated from discharge port 40 and the outlet conduit 14 connected to catheter 18. The patient is thereby safely protected against being inadvertently administered a dangerous dosage of carbon dioxide directly from the source.

After the gas is transferred from reservoir syringe 80 to push-draw syringe 84, the operator manipulates valve lever 67 to rotate stopcock 59 to the third position, which is represented by the stopcock channel in position 61c. Therein, channel segment 63 is communicably aligned with port 48 and channel segment 65 is similarly aligned with channel segment 40. To administer the $CO_2$ in syringe 84 to the patient, plunger 83 of syringe 84 is depressed in the direction of arrow 96. Gas is thereby delivered through port 48 and stopcock channel into port 40. From there, the gas passes in the direction indicated by arrow 58 through one-way valve 54 and into tubing 60. $CO_2$ is thereby transmitted in the direction indicated by arrow 58 through one-way valve 54 and into tubing 60 of outlet section 14. One-way valve 54 prevents backflow of gas into the K-valve assembly.

Lever 67 may be configured as an arrow or otherwise marked to include an arrow that points in the direction of the intended fluid flow. With the lever pointing toward reservoir 80, as shown in FIG. 1, the angled channel 61 is in the position shown in FIG. 2 and fluid flow is directed toward reservoir 80. Alternatively, the lever may be rotated to point toward syringe 84. In this position, the channel is in the position 61b shown in FIG. 2 and $CO_2$ is directed from syringe 80 to a syringe 84. Finally, in the third stage of the process, lever 67 may be directed to point toward the discharge end of port 40 and the attached outlet section 14. In this stage, angled channel 61 is directed to the position 61c, shown in FIG. 2, such that fluid flow is directed from reservoir 84 to the outlet section 14.

$CO_2$ is delivered through tube 60 and into downstream valve 64. Once again, a one-way valve 66 prevents the backflow of gas into the tubing. Stopcock 70 is operated, as required, to either direct the $CO_2$ to catheter 18 and thereby to the patient, or to purge the gas through port 72. The G-tube seal 73 prevents air from entering the line.

Accordingly, system 10 enables controlled amounts of $CO_2$ to be delivered to the patient in a safe and reliable manner. After the components are connected, they may remain connected during the entire medical procedure and do not then have to be disconnected and reconnected. This minimizes the possibility that air will intrude into the system and endanger the patient. Controlled and precise dosages of $CO_2$ are delivered, by the simple and foolproof operation of valve 16, from reservoir syringe 80 to push-draw syringe 84 and then to the patient. At each stage of the process, the inlet and outlet ends of the valve remain totally isolated from one another so that the risk of administering an explosive and potential deadly dose of $CO_2$ is eliminated.

Figure 3:
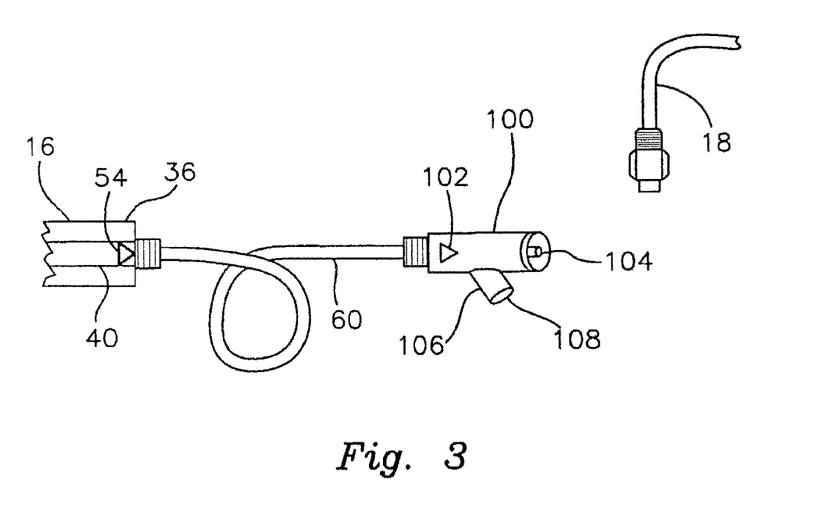
FIG. 3 is a simplified, schematic view of the outlet conduit and an alternative downstream fitting that may be used to interconnect the outlet conduit to the patient catheter.

FIG. 3 again discloses the discharge branch 36 of valve assembly 16. A one-way valve 54 is again installed in port 40 to prevent backflow of gas into valve assembly 16. In this version, tube 60 is communicably connected between discharge branch 36 and a fitting 100 that may be used selectively to perform various functions. In particular, fitting 100 includes a one-way valve 102 that prevents backflow of gas into tube 60. Fitting 100 includes a Luer™ fitting 104 that allows fitting 100 to be releasably attached to catheter 18. A flush port 106 is communicably joined with fitting 100 and features a G-valve seal 108 that permits a syringe (not shown) to be interconnected to port 106. This syringe may be used to administer medications through fitting 100 to attached catheter 18. As a result, such medications may be administered to the patient without having to disconnect the individual components of the fluid delivery system. This saves valuable time in a surgical or medical environment and reduces the risk that air will be introduced into the system. A syringe may also be attached to port 106 to purge or flush the catheter as needed or desired.

Figure 4:
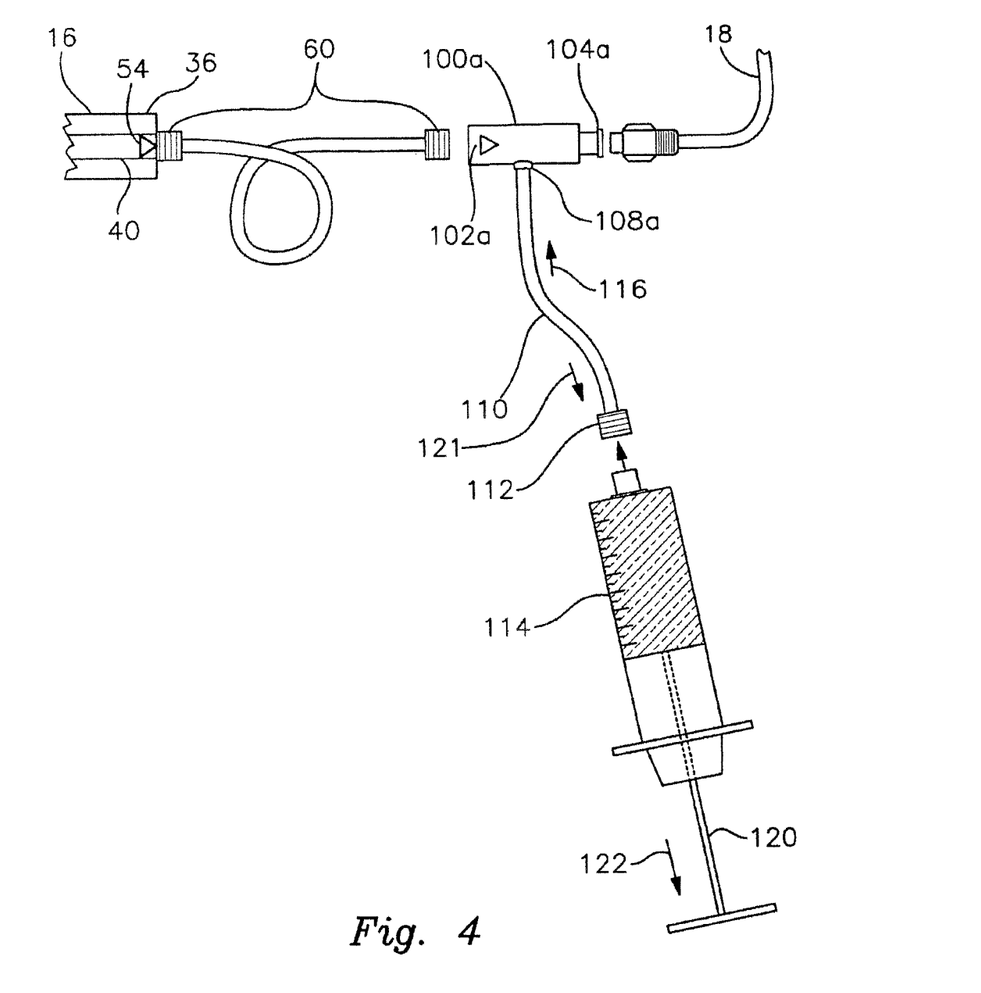
FIG. 4 is a view similar to that of FIGS. 1-3 which depicts a medication administering syringe being attached to the downstream fitting by means of a connecting tube.

FIG. 4 depicts still another embodiment of this invention wherein medical tube 60 is communicably interconnected between the discharge branch 36 of valve assembly 16 and a fitting 100a. The downstream fitting again includes a one-way valve 102a for preventing the backflow of gas or medication into tube 60. A Luer™ fitting 104a releasably interconnects fitting 100a to catheter 18. An inlet/discharge port 108a is formed in fitting 100a for selectively introducing medication into the patient catheter through fitting 100a or alternatively purging or flushing the catheter as required. A line 110 is communicably connected to port 108a and carries at its opposite end a Luer™ fitting 112 for releasably attaching the line to a syringe 114. The syringe is attached to line 100 through fitting 112 in order to optionally deliver medication to catheter 18 through fitting 100a in the direction indicated by arrow 116. Alternatively, fluid may be purged or flushed in the direction of arrow 121 from the catheter and/or from the system through line 110 by drawing plunger 120 of syringe 114 rearwardly in the directions indicated by arrow 122.

In alternative versions of this invention, medical fluid may be transmitted from a source to a patient in multiple stages, as described above, but utilizing multiple valves joined to respective syringes. In particular, in a first stage operation, gas or other fluid under pressure is delivered from the source through a first directional valve to a reservoir syringe communicably connected to the first valve. The reservoir syringe is also connected through the first valve to a second valve which is, in turn, communicably joined to a second syringe. The first valve is operated so that the reservoir syringe remains isolated from the second valve as fluid is delivered from the source to the first syringe through the first valve. When a selected volume of fluid is accommodated by the first syringe, the first valve is operated to connect the first syringe with the second valve. The second valve itself is operated to communicably connect the first syringe to the second syringe while, at the same time, isolating the second syringe from the patient. The second syringe is a push-draw syringe. The first syringe is operated with the second valve in the foregoing position to transmit the fluid from the first syringe to the second syringe. During this stage of the operation, both syringes remain isolated from the source and the patient. As a result, even if fluid under pressure is "stacked" in the reservoir syringe, this pressure is not delivered to the patient. Rather, the desired volume of the fluid is delivered instead to the push-draw syringe. The second valve is then operated to communicably join the push-draw syringe to the patient/patient catheter. Once again, the patient/catheter are totally isolated from the source of fluid under pressure. As a result, a safe and selected volume of fluid is delivered from the push-draw syringe to the patient.

Various valve configurations and types of directional valve may be employed to perform the multi-stage delivery described above. In all versions of this invention, it is important that fluid first be delivered from a fluid source to a first syringe and then delivered sequentially to a second syringe. Ultimately, the fluid in the second, push-draw syringe is delivered sequentially to the patient. During each stage of the process, the source of fluid remains isolated from the patient. Typically, only one stage of the system operates at any given time.

Figure 5:
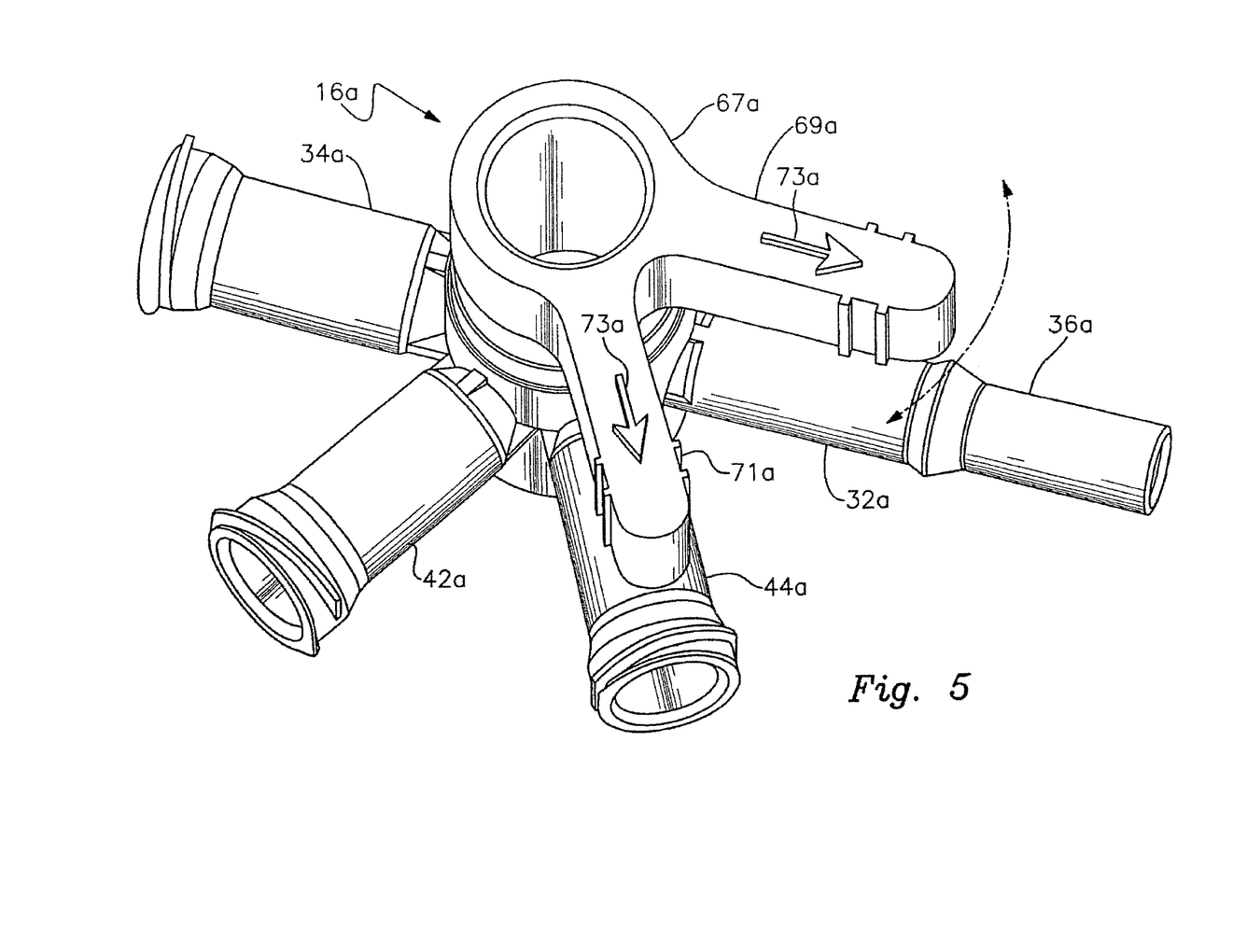
FIG. 5 is a perspective view of a control valve assembly featuring a dual handle for operating the stopcock and indicating which pair of flow ports are open.

There is shown in FIG. 5 an alternative control valve assembly 16a, which again features a generally K-shaped valve body 32a composed of materials similar to those previously described. Aligned inlet and outlet conduit segments 34a and 36a, as well as transverse or angled conduit segments 42a and 44a are selectively interconnected to communicate and transmit fluid flow through respective pairs of the conduits by a rotatable stopcock valve analogous to that disclosed in the previous embodiment. In this version, the stopcock is rotated by a dual handle lever 67a, which includes elongate handles 69a and 71a. These handles diverge from the hub of the stopcock lever at an angle of approximately 60 degrees, which matches the angle between each adjacent pair of fluid transmitting conduits 34a, 42a, 44a and 36a in control valve 16a. Each of handles 69a and 71a is elongate and carries a respective directional arrow 73a that is printed, embossed or otherwise formed along the handle.

Valve lever 67a is turned to operate the stopcock such that a selected pair of adjoining conduits or ports are communicably interconnected to permit fluid flow therethrough. In particular, the stopcock is constructed such that the handles 69a and 71a are aligned with and extend along respective conduits that are communicably connected by the stopcock. In other words, the valve lever 67 is axially rotated until handles 69a and 71a are aligned with adjoining conduits through which fluid flow is required. The angle between the handles matches the angle between the adjoining conduits, e.g. 60 degrees. Lever 67a may therefore be rotated to align diverging handles 69a and 71a respectively with either conduits 34a and 42a, 42a and 44a, or 44a and 36a. In FIG. 5, the handles are aligned with conduits 44a and 36a, and arrows 73a point in a direction that is substantially aligned with those conduits. This indicates that the valve lever 67a is rotated and adjusted such that fluid is able to flow through valve body 32a from transverse conduit 44a to outlet conduit 36a. The valve lever is rotated to selectively align with the other pairs of conduits and thereby open the fluid flow between the selected pair. The use of a dual handle valve lever 67a clarifies and facilitates usage of the control valve assembly. Otherwise, the valve lever employed in the version of FIG. 5 is constructed and operates analogously to the valve lever disclosed in FIGS. 1-3.

Figure 6:
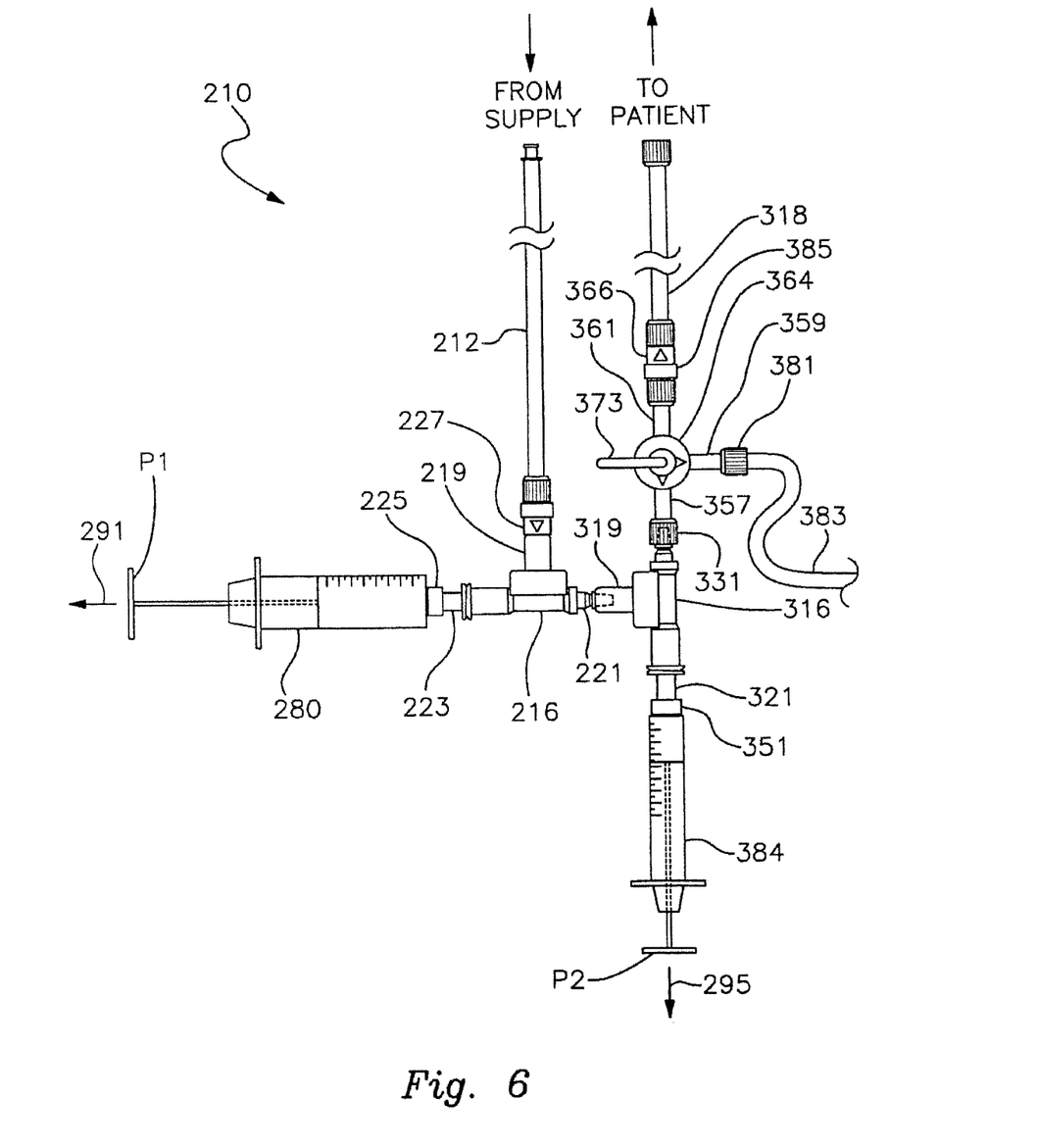
FIG. 6 is an elevational and partially schematic view of an alternative system in accordance with this invention utilizing a pair of multidirectional valves for the control valve assembly.
Figure 7:
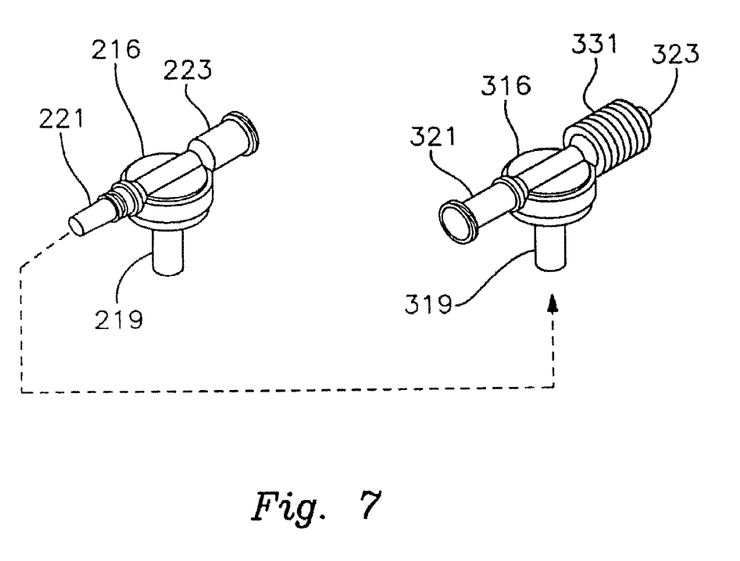
FIG. 7 is a perspective view of the multidirectional valves used in the embodiment of FIG. 5.

FIG. 6 depicts a system 210 in accordance with this invention wherein the control valve assembly comprises a pair of multidirectional valves 216 and 316, shown individually in FIG. 6. These valves are utilized to perform multi-stage delivery of a medical gas such as $CO_2$ or other medical fluid to a patient in a manner analogous to that previously described. Valves 216 and 316 comprise standard multidirectional valves of the type manufactured by Value Plastics, which are suitable for use in medical applications. Such valves respond automatically to a predetermined fluid pressure by allowing fluid flow through at least one path of the valve and restricting such flow through at least one other path of the valve. The construction of such multidirectional valves will be understood to persons skilled in the art.

Valve 216 includes ports 219, 221 and 223 that are communicably interconnected in a T-shaped configuration. Valve 316 similarly includes ports 319, 321 and 323 that are communicably interconnected in a T-shaped configuration. Port 323 comprises a Luer connector having a locking nut 331 carried thereon.

More particularly, port 223 of valve 216 typically comprises a male Luer fitting that is attached to a Luer lock 225 carried at the discharge end of a first, reservoir syringe 280. Inlet port 219 is interconnected through a one way check valve 227 to an inlet conduit 212. The opposite end of that inlet conduit is communicably joined to a pressurized supply of medical fluid in a manner analogous to that previously described. Third port 221 of valve 216 is press fit into port 319 of second multidirectional valve 316. Port 321 of valve 316 is attached to a Luer lock 351 formed at the discharge end of a second, push-draw syringe 384. Locking nut 331 of Luer outlet port 323 allows valve 316 to be connected to a complementary Luer fitting 357 of a downstream directional valve 364. The downstream directional valve comprises a rotary valve that also includes ports 359 and 361. These ports are selectively interconnected to port 357 within the body of valve 364 and collectively define a T-shaped configuration. A directional valve lever 373 is rotated as needed to communicably align two of the respective ports. More particularly, the handle of the lever is directed along and aligned with a selected one of the ports 357, 359 and 361 to close that port such that the other ports communicate in a known manner.

Port 359 of valve 364 is itself communicably interconnected through a standard Luer fitting 381 to a line 383. Port 361 is likewise communicably joined through a Luer fitting 385 to a one-way directional valve 366, which is itself connected to an outlet conduit, i.e. a catheter 318, leading to the patient.

Downstream directional valve 364 is operated, as required, to either bleed or purge excess gas from system 210 (i.e. by turning handle 373 upwardly and aligning it with port 361) or to deliver a selected medication dosage, contrasting agent or other radioscopic substance to the patient (i.e. by rotating handle 373 downwardly and aligning it with port 357 so that line 383 and catheter 318 are communicably joined). Downstream directional valve 364 is adjusted in a rotatable manner that will be known to persons skilled in the art. That valve may be utilized for various functions within the scope of this invention. It should also be understood that various other types of locking, sealing and/or communicative connections may be employed between the respective components of system 210.

System 210 is operated to deliver medical gas or other fluid to a patient in the following manner. In a first stage operation, gas or other fluid under pressure is delivered from the source or supply (as previously described) to reservoir syringe 280 by connecting the supply to conduit 212 and opening the supply. $CO_2$ or other medical fluid under pressure is delivered through inlet conduit 212 and check valve 227 into port 219 of multidirectional valve 216. The multidirectional valve is constructed and operates in a known manner such that the pressurized medical fluid effectively opens the valve to interconnect ports 219 and 223. The fluid therefore is transmitted through Luer fitting 225 into the reservoir of first syringe 280 and the plunger P1 of the syringe retracts in the direction of arrow 291.

When reservoir syringe 280 is filled, the operator depresses plunger P1 in a conventional manner. This pushes the fluid from the reservoir of syringe 280 back through port 223 of valve 216. The pressure created by depressing the plunger P1 causes multidirectional valve 216 to open a communicating pathway between port 223 and aligned port 221. The medical fluid from first syringe 280 is thereby pushed through valve 216 and delivered from port 221 to port 319 of second multidirectional valve 316. At the same time, check valve 227 prevents fluid from being transmitted back through inlet conduit 212 to the gas or liquid supply.

When fluid under pressure is delivered through port 319 to valve 316, the second multidirectional valve opens a communicating pathway between ports 319 and 321. The medical fluid is accordingly transmitted through those interconnected ports and through Luer fitting 351 to the reservoir of second, push-draw syringe 384. In the second stage of the process, the fluid is delivered from first syringe 280 to second syringe 384 while remaining isolated from the fluid supply. The plunger P2 of the second syringe retracts in the direction of arrow 295 as its reservoir is filled. Valve 316 restricts the flow of fluid during this stage to the pathway defined by interconnected and communicating conduits 319 and 321.

The third stage of the process is completed by depressing plunger P2. This causes valve 316 to open a communicating flow path between ports 321 and 323 and restricts the gas or liquid from being transmitted back through port 319. Valve 316 transmits the fluid from syringe 384 through downstream directional valve 364 and check valve 366 to catheter 318. During this third stage of the process, handle 373 is typically pointed toward and aligned with port 359 so that ports 357 and 361 of valve 364 are communicably connected. Handle 373 is depicted as pointed in a "nine o'clock" position in FIG. 6 for purposes of clarity and in order to better illustrate the ports of valve 364. By operating syringe 384, a selected dosage of medical gas or liquid is delivered through catheter 318 to the patient.

Valve 364 is operated, in a manner previously described, to perform desired functions in connection with a radioscopic procedure. For example, to add a medication or radioscopic compound (such as a contrasting substance), handle 373 is typically pointed downwardly (in a "six o'clock" position) so that ports 359 and 361 are communicably joined. The desired substance to be added is then introduced through line 383 and valve 364 to catheter 318, and is thereby administered to the patient. Alternatively, gas may be purged or bled from the system by turning handle 373 such that it points toward and is aligned with port 361 and catheter 318. This communicably interconnects ports 357 and 359 so that excess gas may be discharged through line 383. Accordingly, in either of the embodiments of this invention, the system may be quickly and conveniently purged and/or medication may be added to the administered gas in a quick and convenient manner. In each case, the system does not have to be disconnected, disassembled and/or reassembled. This saves considerable time and effort and greatly reduces the possibility of air intruding into the system.

System 210 may be modified to include particular features and components as described in the embodiment of FIGS. 1-4. In addition, the particular means of component interconnection, sealing, and valve operation may be modified in a manner that will be understood by persons skilled in the art in order to obtain the manner of operation and resulting benefits exhibited by this invention.

The use of multiple syringes is particularly critical and eliminates the risk of stacking that often occurs when a medical fluid is delivered under pressure directly from a source of fluid to a single delivery syringe. In that case, the syringe may be filled with fluid that exceeds the nominal volume of the syringe due to pressure stacking. If such fluid were to be delivered directly to the patient, this could result in a potentially dangerous overdose or fluid flooding. By transmitting the fluid from a reservoir syringe into a second, push-draw syringe, the pressure is equalized and only the fluid volume and pressure accommodated by the second syringe are delivered safely to the patient.

From the foregoing it may be seen that the apparatus of this invention provides for a system for safely delivering a controlled volume of a medical fluid to a patient and, more particularly to a system for delivery a controlled flow of carbon dioxide ($CO_2$) or other contrast media in order to obtain radiological images. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

Other embodiments will occur to those skilled in the art and are within the following claims:

What is claimed is:

1. A system for controlled delivery of a medical liquid or gas from a source of such liquid or gas to a patient, said system comprising:

an inlet conduit for being communicably joined to a source of the medical liquid or gas;

an outlet conduit for being communicably joined to the patient;

first and second receptacles intermediate said inlet and outlet conduits; and a control valve assembly interconnecting said inlet conduit, said outlet conduit, said first receptacle and said second receptacle, said control valve assembly being alternatable between various states comprising a first state wherein said inlet conduit communicates with said first receptacle for transmitting liquid or gas from the source to only said first receptacle, a second state wherein said first receptacle communicates only with said second receptacle and is isolated from said inlet and outlet conduits for transmitting liquid or gas from said first receptacle to only said second receptacle, and a third state wherein said second receptacle communicates only with said outlet conduit and is isolated from said inlet conduit and said first receptacle for transmitting liquid or gas from said second receptacle to only said outlet conduit;

said control valve assembly includes a valve body having aligned inlet and outlet ports, said inlet port being communicably connectable to said inlet conduit and said outlet port being communicably connectable to said outlet conduit, said valve body further including a first intermediate port to which said first receptacle is selectively connected and a second intermediate port to which said second receptacle is selectively connected, said control valve assembly further including a stopcock element mounted rotatably within said body and including a channel comprising a first channel segment and a second channel segment, said first and second channel segments being selectively alignable with said inlet port and said first intermediate port to allow for communication between said inlet conduit and said first receptacle, said first intermediate port and said second intermediate port to allow for communication between said first receptacle and said second receptacle, and said second intermediate port and said outlet port to allow for communication between said second receptacle and said outlet conduit, wherein a longitudinal axis of said inlet port and a longitudinal axis of said first intermediate port define a first angle, said longitudinal axis of said first intermediate port and a longitudinal axis of said second intermediate port define a second angle, and said longitudinal axis of said second intermediate port and a longitudinal axis of said outlet port define a third angle, said first, second, and third angles being approximately the same such that said first and second channel segments of said stopcock are communicably and selectively interchangeable with pairs of adjoining ports in said first state, said second state, and said third state.

2. The system according to claim 1, wherein said first channel segment and said second channel segment are at an acute angle to one another.

3. The system according to claim 2, wherein in said first state, said first channel segment and said second channel segment communicably interconnect said inlet port and said first intermediate port whereby liquid or gas introduced in said inlet conduit is transmitted through said inlet port, said channel and said first intermediate port to said first receptacle.

4. The system according to claim 2, wherein in said second state, said stopcock element aligns said first channel segment and said second channel segment with said first and second intermediate ports respectively to isolate liquid or gas in said first receptacle from both said inlet and outlet conduits and for directing liquid or gas from said first receptacle through said first intermediate port, said channel and said second intermediate port into said second receptacle.

5. The system according to claim 2, wherein in said third state, said stopcock element aligns said first channel segment and said second channel segment with said second intermediate port and said outlet port, respectively to isolate the liquid or gas in said second receptacle from said source, said inlet port and said first intermediate port and for transmitting the liquid or gas through said second intermediate port, said channel and said outlet port to said outlet conduit.

6. The system according to claim 2, wherein said first channel segment and said second channel segment have respective longitudinal axes that form an angle of substantially 60 degrees.

7. The system according to claim 1, wherein said inlet and outlet ports include respective longitudinal axes that are aligned.

8. The system according to claim 1, wherein said first and second intermediate ports include respective longitudinal axes that form an angle of substantially 60 degrees with one another.

9. The system according to claim 1, wherein said first intermediate port forms an axial angle of substantially 60 degrees with the longitudinal axis of said inlet port and wherein the longitudinal axis of said second intermediate port forms an angle of substantially 60 degrees with the longitudinal axis of said outlet port.

10. The system according to claim 1, further including a first one-way valve at said inlet port for restricting liquid or gas flow to a single direction from the source of liquid or gas to said control valve assembly and a second one-way valve at said outlet port for restricting the flow of liquid or gas in a single direction from the control valve assembly through the outlet conduit to the patient.

11. The system according to claim 1, further including a downstream valve connected to said outlet conduit for at least one of bleeding liquid or gas from said system and administering an additive liquid or gas to the medical fluid transmitted through said outlet conduit.

12. The system according to claim 1, wherein said stopcock element is rotated by an attached lever having a pair of diverging handles that are alignable with respective ports of said valve body to indicate that said respective ports are communicatively connected by said channel of said stopcock element.

* * * * *